United States Patent [19]

Freedman

[11] 3,993,757

[45] Nov. 23, 1976

[54] METHOD OF TREATING INFLAMMATION WITH MORPHANTHRIDINES

[75] Inventor: Jules Freedman, Thiensville, Wis.

[73] Assignee: Richardson-Merrell Inc., Wilton, Conn.

[22] Filed: June 6, 1975

[21] Appl. No.: 584,587

[52] U.S. Cl. .............................. 424/244; 424/248; 424/250; 424/274
[51] Int. Cl.² ................ A61K 31/33; A61K 31/40; A61K 31/495; A61K 31/535
[58] Field of Search ............ 424/244, 250, 274, 248

[56] References Cited
UNITED STATES PATENTS

| | | |
|---|---|---|
| 3,153,652 | 10/1964 | Drukker et al. .................... 424/267 |
| 3,267,094 | 8/1966 | Drukker et al. .................... 424/250 |
| 3,370,058 | 2/1968 | Judd et al. .......................... 424/244 |
| 3,692,906 | 9/1972 | Dage .................................. 424/244 |

Primary Examiner—Stanley J. Friedman
Attorney, Agent, or Firm—George W. Rauchfuss, Jr.; Eugene O. Retter; L. Ruth Hattan

[57] ABSTRACT

The inventive method comprises administering a morphanthridine to an animal to effect the lowering of inflammation. Representative of the compounds that can be used in the method are trans-5-acetyl-2-bromo-5,6-dihydro-11-(3-dimethylaminopropylidene)-morphanthridine and trans-2-bromo-11-(3-dimethylaminopropylidene)-5,6-dihydro-5-propionylmorphanthridine.

3 Claims, No Drawings

METHOD OF TREATING INFLAMMATION WITH MORPHANTHRIDINES

BACKGROUND OF THE INVENTION

The 5-acyl morphanthridines are disclosed in U.S. Pat. No. 3,370,058, which issued Feb. 20, 1968. The compound 2-bromomorphanthridine-6(5H)-11-dione has been reported by W. S. Waring and B. A. Whittle in *J. Pharm. Pharmacol.*, 21, 520 (1969). Related compounds are disclosed in U.S. Pats. Nos. 3,692,906; 3,267,094; and 3,153,652. None of the above references discloses the use of morphanthridines as anti-inflammatory agents.

DESCRIPTION OF THE INVENTION

The present invention relates to a method of treating inflammation in animals by administering to the animals a trans isomer of morphanthridine of the formula:

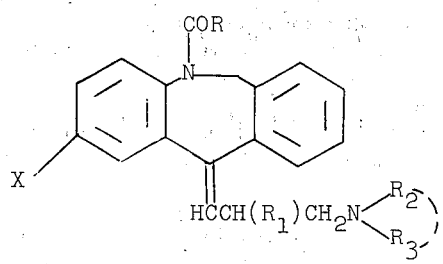

I in which X is hydrogen, a halogen such as chlorine, bromine or fluorine, trifluoromethyl, a lower alkyl of 1 to 4 carbon atoms, or a lower alkoxy of 1 to 4 carbon atoms, R is hydrogen or an alkyl of 1 to 8 carbon atoms such as methyl, ethyl, isopropyl, butyl, hexyl or octyl, $R_1$ is hydrogen or methyl, and $R_2$ and $R_3$ are selected from hydrogen, a lower alkyl of 1 to 4 carbon atoms or a phenyl-lower alkyl of 7 to 13 carbon atoms such as benzyl, phenethyl or phenyl-isopropyl. $R_2$ and $R_3$ may be joined together by an alkylidene group to form a heterocyclic amino group such as morpholino, pyrrolidino, piperadino, N-lower alkyl piperazino such as N-methylpiperazino, N-phenyl-lower alkyl piperazino such as N-benzylpiperazino, or N-(hydroxy-lower alkyl)-piperazino such as 4-hydroxyethylpiperazino.

In the preferred practice of the invention the animal suffering from inflammation is administered a safe and effective amount of a trans isomer of a 5-acyl morphanthridine in the form of its free base or in the form of a non-toxic acid addition salt.

It has been discovered that the trans isomer of the 5-acyl morphanthridines possesses useful anti-inflammatory activity and the cis isomer does not. The active ingredient is preferably combined with one or more diluents and formed into unit dosage forms for oral or parenteral administration.

The compounds of Formula I may be prepared as described in U.S. Pat. No. 3,370,058, or they may be prepared by the method employed in the examples. The method employed in the examples is preferred as it results in good yields of the trans isomer in a form which is substantially free of the inactive cis isomer. That method may be illustrated as follows:

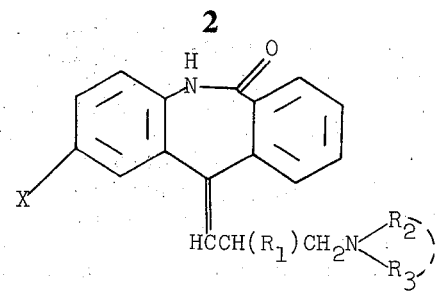

II (1) $AlH_3$
(2) Acetonitrile
(3) Separate isomers

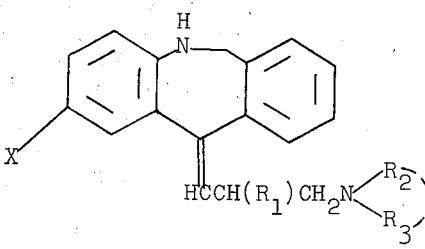

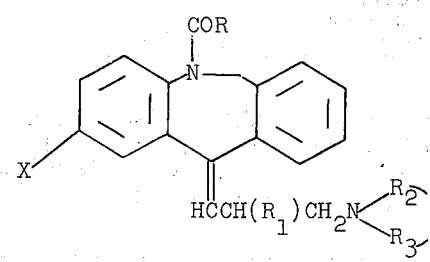

Representative of the compounds which may be employed in the method of the present invention are trans isomers of the following:

5-acetyl-2-bromo-5,6-dihydro-11-(3-dimethylaminopropylidene)morphanthridine,
2-bromo-11-(3-dimethylaminopropylidene)-5,6-dihydro-5-propionylmorphanthridine,
5-acetyl-11-(N-methyl-4-piperidylene)-5,6-dihydromorphanthridine,
5-acetyl-11-(N-ethyl-3-piperidylene)-5,6-dihydromorphanthridine,
5-propionyl-11-(N-benzyl-3-pyrrolidylene)-5,6-dihydromorphanthridine,
5-butyryl-11-(N-allyl-3-homopiperdiylene)-5,6-dihydromorphanthridine,
5-acetyl-11-(3-dimethylaminopropylidene)-5,6-dihydromorphanthridine, 2-chloro-5-acetyl-11-(3-dimethylamino-
propylidene)-5,6-dihydromorphanthridine, 5-acetyl-11-(2-diethylaminopropylidene)-5,6-dihydromorphanthridine, 2-chloro-5-acetyl-11-(3-dimethylamino-2-methylpropylidene)-5,6-dihydromorphanthridine, and 5-propionyl-11-(diallylaminopropylidene)-5,6-dihydromorphanthridine.

The compound trans-5-acetyl-2-bromo-5,6-dihydro-11-(3-dimethylaminopropylidene)morphanthridine is representative of the compounds that can be employed in the forementioned invention. The anti-inflammatory activity of the compound was investigated on rats by the carrageenan edema test using the method of Winter, et al. (J. Pharmacol. Exp. Ther., 141, 369/1963). Male rats weighing 125–150 g. were used as test animals and 0.05 ml. doses of a 1% carrageenan suspension were injected subcutaneously into the hind paws of the animals. The thus provoked edema was measured by means of mercury displacement. The compound demonstrated good anti-inflammatory activity at a dose of 80 mg/kg orally. Further anti-inflammatory testing against mycobacterial-induced arthritis demonstrated that the compound had a good dosedependent anti-inflammatory activity. In other tests, the compound was determined to have an $LD_{50}$ of 175 mg/kg intraperitoneally.

Representative of the suitable pharmaceutical compositions that may be employed in the practice of the invention are the following:

TABLETS

| | Mg. |
|---|---|
| (1) trans-5-acetyl-2-bromo-5,6-dihydro-11-(3-dimethylaminopropylidene)morphanthridine | 50 |
| (2) Starch, U.S.P. | 57 |
| (3) Lactose, U.S.P. | 43 |
| (4) Talc, U.S.P. | 9 |
| (5) Stearic acid | 6 |

Powders (1), (2) and (3) are slugged, then granulated, mixed with (4) and (5) and tableted.

Capsules may be prepared by filling No. 3 hard gelatin capsules with the following ingredients:

CAPSULES

| | Mg. |
|---|---|
| (1) trans-5-acetyl-2-bromo-5,6-dihydro-11-(3-dimethylaminopropylidene)morphanthridine | 50 |
| (2) Lactose, U.S.P. | 150 |
| (3) Starch, U.S.P. | 16 |
| (4) Talc, U.S.P. | 8 |

The oral route is generally preferred for administering the compounds of this invention. However, other routes of administration such as parenteral may be employed.

In the preferred practice of the invention the patients will receive daily doses of from 50 mg. to 500 mg. of the active ingredient. The doses to be administered to a specific patient will, of course, depend upon many factors, including the patient's overall condition. Generally speaking, however, the daily doses will not normally exceed 175 mg/kg of body weight intraperitoneally. The oral dose will run somewhat higher and the intravenous doses somewhat lower.

The following examples illustrate the preparation of representative compounds which may be employed in the practice of the invention.

EXAMPLE 1 trans-2-Chloro-11-(3-dimethylaminopropylidene)-5,6-dihydromorphanthridine

A solution of the isomers of 2-chloro-11-(3-dimethylaminopropylidene)morphanthridine-6(5H) one (88.1 g., 0.27 M) in 800 ml. of tetrahydrofuran is added dropwise to a suspension of 16.0 g. (0.41 M) of lithium aluminum hydride in 700 ml. of tetrahydrofuran. The mixture is stirred and refluxed for six hours, cooled in ice and decomposed by dropwise addition of 60 ml. of 40% potassium hydroxide. The solids are filtered and the solvent removed from the filtrate. The residue is dissolved in 500 ml. of hot acetonitrile and refrigerated. The precipitate of the cis-isomer is filtered and the solvent removed to leave a residue of the trans-isomer. The latter solidifies and is recrystallized twice from methylcyclohexane to yield trans-2-chloro-11-(3-dimethylaminopropylidene)-5,6-dihydromorphanthridine, m.p. 102°–104°.

Anal. Calcd. for $C_{19}H_{21}ClN_2$: C, 72.94; H, 6.76; Cl, 11.34; N, 8.96. Found: C, 72.98; H, 6.87; Cl, 11:22; N, 8.99.

EXAMPLE 2 trans-2-Chloro-11-(3-dimethylaminopropylidene)-5,6-dihydro-5-formylmorphanthridine A mixture of 6.26 g. (0.02 M) of trans-2-chloro-11-(3-dimethylaminopropylidene)-5,6-dihydromorphanthridine, and 25 ml. of 89% formic acid is refluxed for thirty minutes, cooled, and poured into ice water. The solution is made alkaline with 40% potassium hydroxide, the oil extracted into ether and the solution washed with dilute hydrochloric acid. After drying over potassium carbonate, the solvent is removed and the residue recrystallized two times from methylcyclohexane to give trans-2-chloro-11-(3-dimethylaminopropylidene)-5,6-dihydro-5-formylmorphanthridine, m.p. 91°–93°.

Anal. Calcd. for $C_{20}H_{21}ClN_2O$: C, 70.47; H, 6.21; N, 8.22. Found: C, 70.51; H, 6.17; N, 8.00.

EXAMPLE 3 trans-5-Acetyl-2-chloro-11-(3-dimethylaminopropylidene)-5,6-dihydromorphanthridine A mixture of 10 g. of trans-2-chloro-11-(3-dimethylaminopropylidene)-5,6-dihydromorphanthridine, and 50 ml. of acetic anhydride is heated on a steam bath for one hour, cooled and poured into 200 ml. of water. The solution is washed with ether and made alkaline with sodium hydroxide solution. The oil is extracted into ether, washed with saturated sodium chloride solution and dried over potassium carbonate. Removal of the ether and Kugelrohr distillation gives trans-5-acetyl-2-chloro-11-(3-dimethylaminopropylidene)-5,6-dihydromorphanthridine, b.p. 130°–140°/0.2 mm.

Anal. Calcd. for $C_{21}H_{23}ClN_2O$: C, 71.08; H, 6.53; Cl, 9.99; N, 7.89. Found: C, 71.03; H, 6.64; Cl, 9.78; N, 8.07.

EXAMPLE 4

2-Bromo-11-(3-dimethylaminopropyl)-11-hydroxymorphanthridine-6(5H) one

To a refluxing suspension of 342 g. (1.14 M) of 2-bromo-6(5H),11-morphanthridine dione in 6.8 liters of tetrahydrofuran is added dropwise the Gringnard reagent prepared from 419 g. (3.45 M) of dimethylaminopropyl chloride, 83.8 g. (3.45 M) of magnesium and 1.37 liters of tetrahydrofuran. A clear solution forms during the addition. After an additional 45 minutes of reflux, the mixture is allowed to come to room temperature overnight. It is then cooled in ice and decomposed with 450 ml. of saturated ammonium chloride. After stirring 2 hours, the solids are filtered and the solvent removed from the filtrate. The residue is triturated with acetonitrile and dried to give 2-bromo-11-(3-dimethylaminopropyl)-11-hydroxymorphanthridine-6(5H)one, m.p. 190°–192°.

Anal. Calcd. for $C_{19}H_{21}BrN_2O_2$: C, 58.63; H, 5.44; Br, 20.53; N, 7.19. Found: C, 58.56; H, 5.49; Br, 20.49; N, 7.19.

EXAMPLE 5

2-Bromo-11-(3-dimethylaminopropylidene)morphanthridine-6(5H)one

2-Bromo-11-(3-dimethylaminopropyl)-11-hydroxymorphanthridine-6(5H)one (15.6 g., 0.04 M) is added in portions to 40 ml. of concentrated sulfuric acid while cooling in ice. The mixture is stirred 0.5 hour in the ice bath at room temperature, then poured on ice. The solution is made basic with sodium hydroxide and the precipitate filtered, dried and recrystallized twice from acetonitrile to give 2-bromo-11-(3-dimethylaminopropylidene)morphanthridine-6(5H)one, m.p. 135°–142°.

Anal. Calcd. for $C_{19}H_{19}BrNO$: C, 61.46; H, 5.16; Br, 21.52; N, 7.54. Found: C, 61.32; H, 5.19; Br, 21.46; N, 7.55.

EXAMPLE 6 trans-2-Bromo-11-(3-dimethylaminopropylidene)-5,6-dihydromorphanthridine

A solution of the isomeric mixture of 2-bromo-11-(3-dimethylaminopropylidene)morphanthridine-6(5H)one (81 g., 0.23 M) in 500 ml. of tetrahydrofuran is added dropwise to a suspension of aluminum hydride prepared from 210 g. (0.54 M) of lithium aluminum hydride, 26.5 g. (0.27 M) of sulfuric acid and 750 ml. of tetrahydrofuran. The mixture is refluxed for 2 hours, cooled in ice and decomposed by dropwise addition of 20% potassium hydroxide. The solids are filtered and the solvent removed from the filtrate. The residue is taken up in hot acetonitrile. The precipitated cis-isomer, m.p. 158°–160°, is filtered and the solvent removed from the filtrate. The residue is purified by silica gel chromatography and recrystallized from methylcyclohexane to give trans-2-bromo-11-(3-dimethylaminopropylidene)-5,6-dihydromorphanthridine, m.p. 103°–107°.

Anal. Calcd. for $C_{19}H_{21}BrN_2$: C, 63.87; H, 5.92; Br, 22.37; N, 7.84. Found: C, 63.77; H, 5.95; Br, 22.45; N, 7.75.

EXAMPLE 7 trans-5-Acetyl-2-bromo-11-(3-dimethylaminopropylidene)-5,6-dihydromorphanthridine A mixture of 7.0 g. (0.019 M) of trans-2-bromo-11-(3-dimethylaminopropylidene)-5,6-dihydromorphanthridine, and 35 ml. of acetic anhydride is heated on a steam bath for 2 hours, cooled and poured into water. When the excess anhydride is decomposed, the solution is made basic with 10% sodium hydroxide, the precipitated oil extracted into ether and the extracts dried over potassium carbonate. Removal of the solvent and distillation in a Kugelrohr apparatus at 145°–150°/0.2 mm. gives trans-5-acetyl-2-bromo-11-(3-dimethylaminopropylidene)-5,6-dihydromorphanthridine.

Anal. Calcd. for $C_{21}H_{23}BrN_2O$: C, 63.15; H, 5.81; N, 7.01. Found: C, 62.99; H, 5.88; N, 6.98.

EXAMPLE 8 trans-2-Bromo-11-(3-dimethylaminopropylidene)-5,6-dihydro-5-propionylmorphanthridine A mixture of 4.7 g. (0.013 M) of trans-2-bromo-11-(3-dimethylaminopropylidene)-5,6-dihydromorphanthridine, and 25 ml. of propionic anhydride is heated in an oil bath at 140° for 1 hour, cooled, and poured into water. The mixture is made basic with excess 10% sodium hydroxide and the precipitated oil extracted into ether. After drying over potassium carbonate, the solvent is removed and the residue distilled in a Kugelrohr apparatus at 145°–155°/0.2 mm. to give trans-2-bromo-11-(3-dimethylaminopropylidene)-5,6-dihydro-5-propionylmorphanthridine.

Anal. Calcd. for $C_{22}H_{25}BrN_2O$: C, 63.92; H, 6.10; Br, 19.33; N, 6.78. Found: C, 63.94; H, 6.13; Br, 19.42; N, 6.81.

EXAMPLE 9

2-Bromo-11-(3-diethylaminopropyl)-11-hydroxymorphanthridine-6(5H)one

A Grignard reagent is prepared from 10.4 g. (0.428 M) of magnesium, 64 g. (0.428 M) of diethylaminopropyl chloride, and 150 ml. of tetrahydrofuran. This reagent is added dropwise to a refluxing suspension of 51.8 g. (0.171 M) of 2-bromomorphanthridine-6(5H),11-dione. After 2 hours reflux, the solution is cooled in ice and decomposed with 100 ml. saturated ammonium chloride. The solids are filtered and the solvent removed from the filtrate. The solid residue (77.2 g.) is dissolved in 1.5 liters of hot ethanol and cooled to give 2-bromo-11-(3-diethylaminopropyl)-11-hydroxymorphanthridine-6(5H)one, m.p. 186°–188°.

Anal. Calcd. for $C_{21}H_{25}BrN_2O_2$: C, 60.43; H, 6.04; Br, 19.15; N, 6.71. Found: C, 60.60; H, 6.10; Br, 19.25; N, 6.80.

EXAMPLE 10

2-Bromo-11-(3-diethylaminopropylidene)morphanthridine-6(5H)one

2-Bromo-11-(3-diethylaminopropyl)-11-hydroxymorphanthridine-6(5H)one (51.7 g., 0.12 M) is stirred for 4.5 hours at room temperature with 125 ml. of concentrated sulfuric acid. The solution is poured on ice and made basic with 10% sodium hydroxide. The semisolid which forms is extracted into ether, the extracts washed with saturated sodium chloride solution, and dried over potassium carbonate. The solvent is removed and the oily residue (55.2 g.) dissolved in 300 ml. of hot acetonitrile. Slow cooling gives 41.1 g. of a white solid, m.p. 115°–122°. A 0.5 g. sample recrystallized from 3 ml. of acetonitrile gives 2-bromo-11-(3-diethylaminopropylidene)morphanthridine-6(5H)-one, m.p. 114°–119°.

Anal. Calcd. for $C_{21}H_{23}BrN_2O$: C, 63.16; H, 5.81; Br, 20.01; N, 7.02. Found: C, 63.27; H, 5.87; Br, 20.16; N, 7.10.

EXAMPLE 11 trans-2-Bromo-11-(3-diethylaminopropylidene)5,6-dihydromorphanthridine

The isomeric mixture of 2-bromo-11-(3-diethylaminopropylidene)morphanthridine-6(5H)one (20.0 g., 0.05 M) in 200 ml. of tetrahydrofuran is added dropwise to a slurry of aluminum hydride in tetrahydrofuran (prepared from 5.3 g. (0.14 M) of lithium aluminum hydride, 6.86 g. (0.07 M) of sulfuric acid, and 400 ml. of tetrahydrofuran). The mixture is refluxed 3 hours, cooled in ice and decomposed with 60ml. of 40% potassium hydroxide. The solids are filtered and the solvent removed from the filtrate. The residual oil is heated with 50 ml. of acetonitrile and 4.81 g. of oxalic acid, and cooled to precipitate the oxalate of the cis-isomer, m.p. 180°–183°.

The solids are filtered and the solvent removed from the filtrate. The base is liberated with sodium hydroxide solution and the oil extracted into ether. After drying over potassium carbonate, the oil is chromatographed on silica gel. Elution with toluene-diethylamine (98:2) gives trans-2-bromo-11-(3-diethylaminopropylidene)5,6-dihydromorphanthridine, which is purified by distillation in a Kugelrohr apparatus at 140°–145°/0.2 mm.

Anal. Calcd. for $C_{21}H_{25}BrN_2$: C, 65.45; H, 6.54; Br, 20.74; N, 7.27. Found C, 65.43; H, 6.53; Br, 20.76; N, 7.26.

EXAMPLE 12 trans-5-Acetyl-2-bromo-11-(3-diethylaminopropylidene)-5,6-dihydromorphanthridine A mixture of trans-2-bromo-11-(3-diethylaminopropylidene)-5,6-dihydromorphanthridine (7.9 g., 0.02 M) and 40 ml. of acetic anhydride is heated on a steam bath for 1.5 hours, cooled, and poured into cold water. The solution is made basic with 10% NaOH and the precipitated oil is extracted into ether. After drying over potassium carbonate, the solvent is removed and the residue distilled in a Kugelrohr apparatus at 145°–155°/0.2 mm. to give trans-5-acetyl-2-bromo-11-(3-diethylaminopropylidene)-5,6-dihydromorphanthridine.

Anal. Calcd. for $C_{23}H_{27}BrN_2O$: C, 64.63; H, 6.37; Br, 18.70; N, 6.56. Found: C, 64.56; H, 6.39; Br, 18.74; N, 6.60.

EXAMPLE 13

2-Bromo-11-hydroxy-11-(3-pyrrolidinopropyl)morphanthridine-6(5H)one

The Grignard reagent prepared from 133 g. (0.9 M) of pyrrolidinopropyl chloride, 21.9 g. (0.9 M) of magnesium, and 1.1 liters of tetrahydrofuran is added to a solution of 90.6 g. (0.3 M) of 2-bromomorphanthridine-6(5H),11-dione in 1.8 liters of tetrahydrofuran. The mixture is refluxed for 1 hour, cooled and decomposed with 115 ml. of saturated ammonium chloride solution. The solids are filtered and the filtrate concentrated. The solid residue is triturated with hot acetonitrile and insolubel solids are filtered to give 2-bromo-11-hydroxy-11-(3-pyrrolidinopropyl)morphanthridine-6(5H)one, m.p. 209°–213°. A sample recrystallized from 30 volumes of tetrahydrofuran has a melting point of 216°.

Anal. Calcd. for $C_{21}H_{23}BrN_2O_2$: C, 60.73; H, 5.58; Br, 19.24; N, 6.75. Found: C, 60.79; H, 5.59; Br, 19.38; N, 6.84.

EXAMPLE 14

2-Bromo-11-(3-pyrrolidinopropylidene)-morphanthridine-6(5H)one oxalate

2-Bromo-11-(3-pyrrolidinopropyl)morphanthridine-6(5H)-one is dehydrated by stirring at room temperature with 300 ml. of concentrated sulfuric acid. Workup gives the lactam as an oil which is purified via the oxalate salt prepared in methanol (93g., m.p. 243°–247°,dec.). A 5.0 g. sample recrystallized from 50 parts of 1:1 methanol-water gives 2-bromo-11-(3-pyrrolidinopropylidene)morphanthridine-6(5H)-one oxalate, m.p. 254°–255° dec.

Anal. Calcd. for $C_{23}H_{23}BrN_2O_5$: C, 56.68; H, 4.76; Br, 16.40; N, 5.75. Found: C, 56.58; H, 4.79; Br, 16.51; N, 5.75.

EXAMPLE 15 trans-2-Bromo-5,6-dihydro-11-(3-pyrrolidinopropylidene)morphanthridine

The base is liberated from 39.0 g. (0.08 M) of the oxalate salt of the isomeric mixture of 2-bromo-11-(3-pyrrolidinopropylidene)morphanthridine-6(5H)one of Example 14 and taken up in 300 ml. of tetrahydrofuran. The solution is added dropwise to a suspension of aluminum hydride in tetrahydrofuran (prepared from 7.59 g. (0.2 M) of lithium aluminum hydride, 9.8 g. (0.1 M) of sulfuric acid, and 500 ml. of tetrahydrofuran). After refluxing 4 hours, the mixture is cooled in ice and decomposed by dropwise addition of 100 ml. of 40% potassium hydroxide. The solids are filtered and the filtrate concentrated. The residues are dissolved in 200 ml. of hot acetonitrile and cooled to give 15.0 g. of trans-2-bromo-5,6-dihydro-11-(3-pyrrolidinopropylidene)morphanthridine, m.p. 136°–139°. Another recrystallization raises the melting point to 138°–139.5°.

Anal. Calcd. for $C_{21}H_{25}BrN_2O_2$: C, 65.80; H, 6.05; Br, 20.85; N, 7.31. Found: C, 65.91; H, 6.10; Br, 20.82; N, 7.32.

EXAMPLE 16 trans-5-Acetyl-2-bromo-5,6-dihydro-11-(3-pyrrolidinopropylidene)morphanthridine

A mixture of 5.0 g. (0.013 M) of trans-2-bromo-5,6-dihydro-11-(3-pyrrolidinopropylidene)morphanthridine and 25 ml. of acetic anhydride is heated on a steam bath for 1 hour and poured into cold water. The solution is made basic with 10% NaOH and the precipitated oil extracted into ether. After drying over magnesium sulfate, the solvent is removed and the residue distilled in a Kugelrohr apparatus at 160°–165°/0.15 mm. to give trans-5-acetyl-2-bromo-5,6-dihydro-11-(3-pyrrolidinopropylidene)morphanthridine.

Anal. Calcd. for $C_{23}H_{25}BrN_2O$: C, 64.94; H, 5.92; Br, 18.79; N, 6.59. Found: C, 64.87; H, 5.92; Br, 18.86; N, 6.59.

I claim:

1. A method of treating inflammation in animals which comprises the step of administering to an animal suffering from inflammation a safe and an anti-inflammatory effective amount of a trans isomer of a compound of the formula:

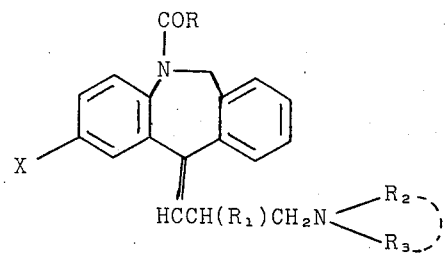
I in which X is hydrogen, a halogen, trifluromethyl, a lower alkyl of 1 to 4 carbon atoms, or a lower alkoxy of 1 to 4 carbon atoms, R is hydrogen or an alkyl of 1 to 8 carbon atoms, $R_1$ is hydrogen or methyl, and $R_2$ and $R_3$ are selected from hydrogen, a lower alkyl of 1 to 4 carbon atoms, or a phenyl-lower alkyl of 7 to 13 carbon atoms, $R_2$ and $R_3$ may be joined together to form a heterocyclic amino group selected from the group consisting of morpholino, pyrrolidino, piperadino, N-lower alkyl piperazino, N-phenyl-lower alkyl piperazino or N-(hydroxy-lower alkyl)-piperazino; or a pharmaceutically acceptable salt thereof.

2. The method of claim 1 in which the compound is trans-5-acetyl-2-bromo-5,6-dihydro-11-(3-dimethylaminopropylidene)morphanthridine.

3. The method of claim 1 in which the compound is trans-2-bromo-11-(3-dimethylaminopropylidene)-5,6-dihydro-5-propionylmorphanthridine.

* * * * *